(12) United States Patent
Kobayashi et al.

(10) Patent No.: US 10,113,947 B2
(45) Date of Patent: Oct. 30, 2018

(54) SEMICONDUCTOR ANALYSIS CHIP AND PARTICLE INSPECTION METHOD

(71) Applicant: KABUSHIKI KAISHA TOSHIBA, Minato-ku, Tokyo (JP)

(72) Inventors: Kentaro Kobayashi, Tokyo (JP); Hiroshi Hamasaki, Hiratsuka Kanagawa (JP); Naofumi Nakamura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 236 days.

(21) Appl. No.: 15/058,896

(22) Filed: Mar. 2, 2016

(65) Prior Publication Data
US 2017/0074824 A1 Mar. 16, 2017

(30) Foreign Application Priority Data

Sep. 11, 2015 (JP) .................................. 2015-179766

(51) Int. Cl.
*G01N 27/453* (2006.01)
*G01N 15/10* (2006.01)
(Continued)

(52) U.S. Cl.
CPC ............ *G01N 15/1031* (2013.01); *B01L 3/00* (2013.01); *B01L 3/502761* (2013.01);
(Continued)

(58) Field of Classification Search
CPC ....... G01N 27/44704; G01N 27/44752; G01N 27/44791; G01N 27/453
See application file for complete search history.

(56) References Cited

U.S. PATENT DOCUMENTS

| 4,908,112 A | * | 3/1990 | Pace | ................. B01L 3/502761 204/601 |
| 7,347,921 B2 | * | 3/2008 | Barth | ................. B01L 3/502761 204/450 |

(Continued)

FOREIGN PATENT DOCUMENTS

| JP | 2001088096 A | 4/2001 |
| JP | 2002005888 A | 1/2002 |

(Continued)

OTHER PUBLICATIONS

JPO computer-generated English langauge translation of JP 2007-021391 A. Downloaded Jan. 12, 2016.*

(Continued)

*Primary Examiner* — Alexander S Noguerola
(74) *Attorney, Agent, or Firm* — Holtz, Holtz & Volek PC

(57) ABSTRACT

According to one embodiment, a semiconductor analysis chip for detecting a particle in a sample liquid includes a semiconductor substrate, a first flow channel provided in a surface portion of the semiconductor substrate, a second flow channel provided in a surface portion of the semiconductor substrate, part of the second flow channel contacting or intersecting the first flow channel, a micropore provided in a contact portion or an intersection of the first and second flow channels, and configured to permit the particle to pass therethrough, a first electrode provided in the first flow channels, a second electrode provided in the second passage, and a third electrode provided in the first flow channel downstream of the first electrode.

18 Claims, 10 Drawing Sheets

(51) Int. Cl.
*G01N 27/447* (2006.01)
*G01N 33/487* (2006.01)
*B01L 3/00* (2006.01)
*G01N 15/12* (2006.01)

(52) U.S. Cl.
CPC ....... *G01N 15/12* (2013.01); *G01N 27/44791* (2013.01); *G01N 33/48721* (2013.01); *B01L 2300/0645* (2013.01); *B01L 2300/0681* (2013.01); *B01L 2300/0816* (2013.01); *B01L 2300/0864* (2013.01); *B01L 2400/0415* (2013.01); *G01N 2015/1006* (2013.01)

(56) References Cited

U.S. PATENT DOCUMENTS

| | | | |
|---|---|---|---|
| 7,410,564 B2* | 8/2008 | Flory | B82Y 10/00 204/403.01 |
| 7,515,268 B1 | 4/2009 | Ayliffe et al. | |
| 2002/0040851 A1 | 4/2002 | McNeil-Watson et al. | |
| 2004/0108208 A1* | 6/2004 | Iida | B01L 3/502761 204/450 |
| 2012/0043202 A1 | 2/2012 | Miyamura et al. | |
| 2014/0158540 A1 | 6/2014 | Ohura | |
| 2014/0252505 A1 | 9/2014 | Kobayashi et al. | |
| 2014/0256028 A1 | 9/2014 | Kobayashi et al. | |
| 2015/0041316 A1 | 2/2015 | Miki et al. | |

FOREIGN PATENT DOCUMENTS

| | | |
|---|---|---|
| JP | 2005098818 A | 4/2005 |
| JP | 2007021391 A | 2/2007 |
| JP | 2007170840 A | 7/2007 |
| JP | 2012255810 A | 12/2012 |
| JP | 2013036865 A | 2/2013 |
| JP | 2014173934 A | 9/2014 |
| JP | 2015036631 A | 2/2015 |
| WO | 2015072186 A1 | 5/2015 |
| WO | 2015129073 A1 | 9/2015 |
| WO | 2016009674 A1 | 1/2016 |

OTHER PUBLICATIONS

JPO computer-generated English langauge translation of JP 2014-173934 A. Downloaded Jan. 12, 2016.*
JPO computer-generated English langauge translation of JP 2015-036631 A. Downloaded Jan. 12, 2016.*
JPO computer-generated English langauge translation of JP 2002-005888 A. Downloaded Jan. 12, 2016.*
Japanese Office Action (and English translation thereof) dated Sep. 20, 2016, issued in counterpart Japanese Application No. 2015-179766.

* cited by examiner

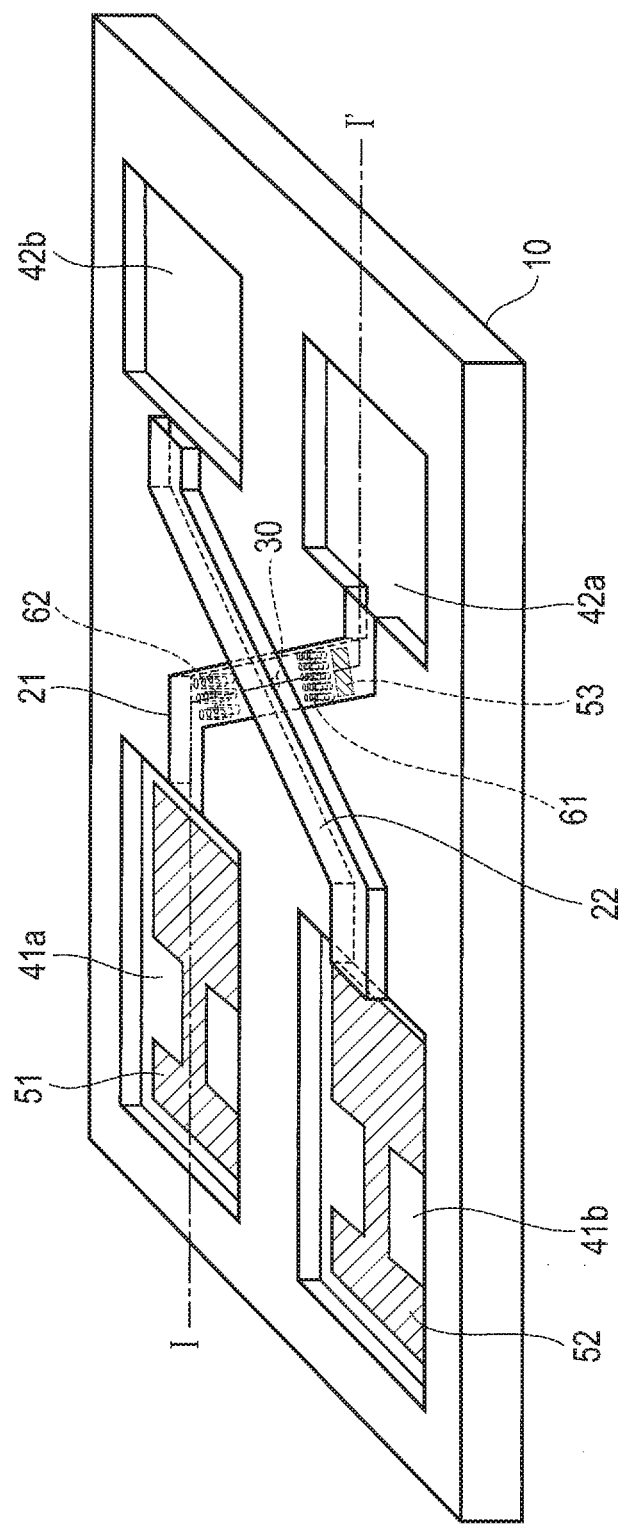
F I G. 2

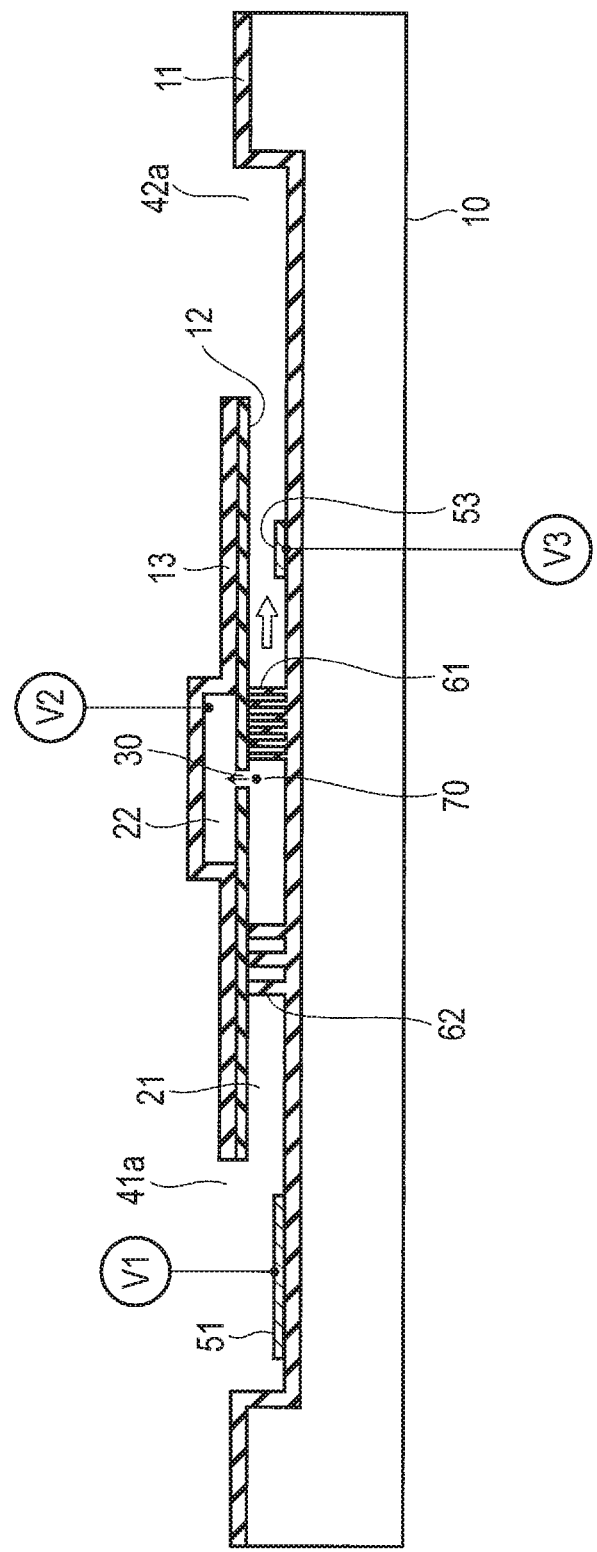
F I G. 3

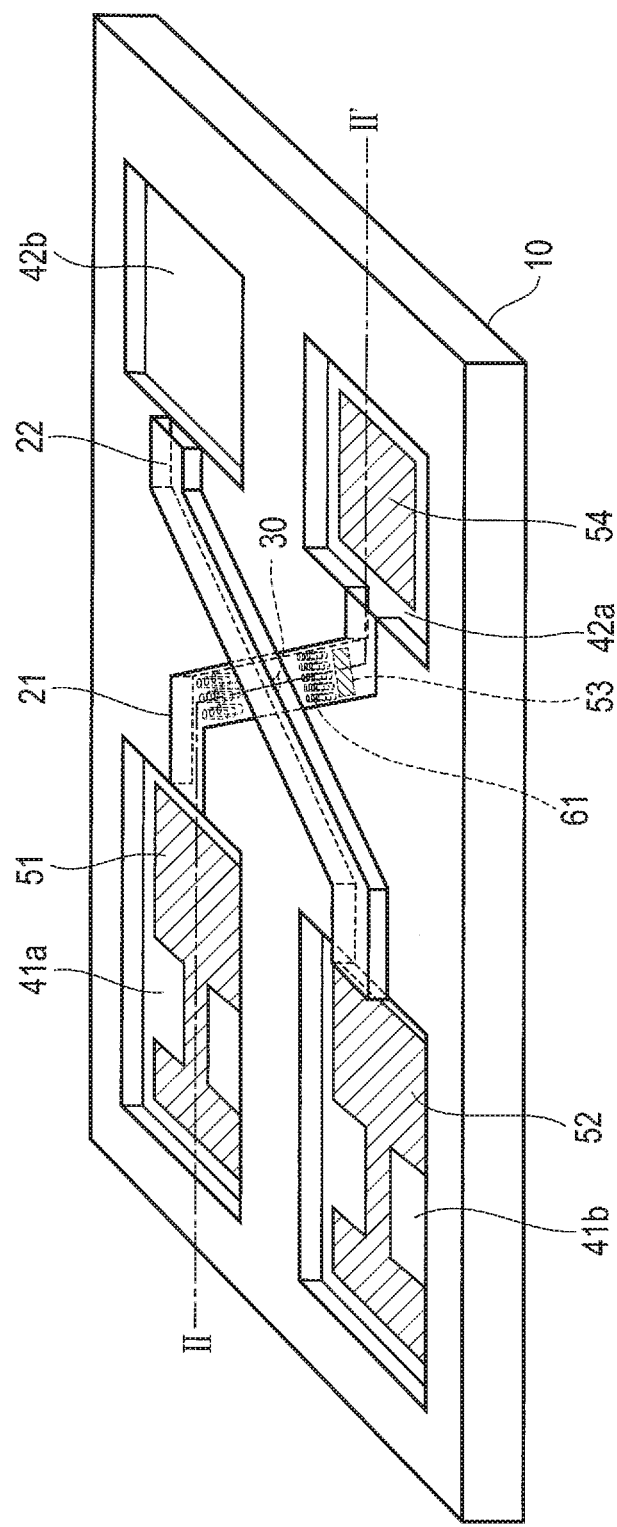
F I G. 6

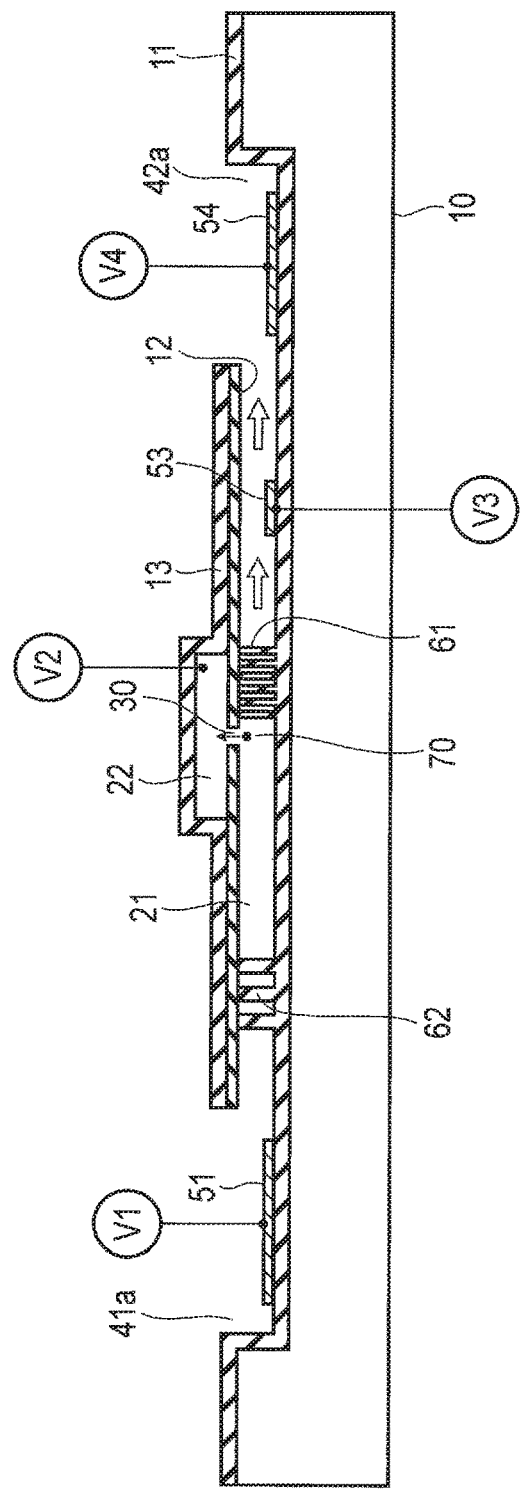
F I G. 7

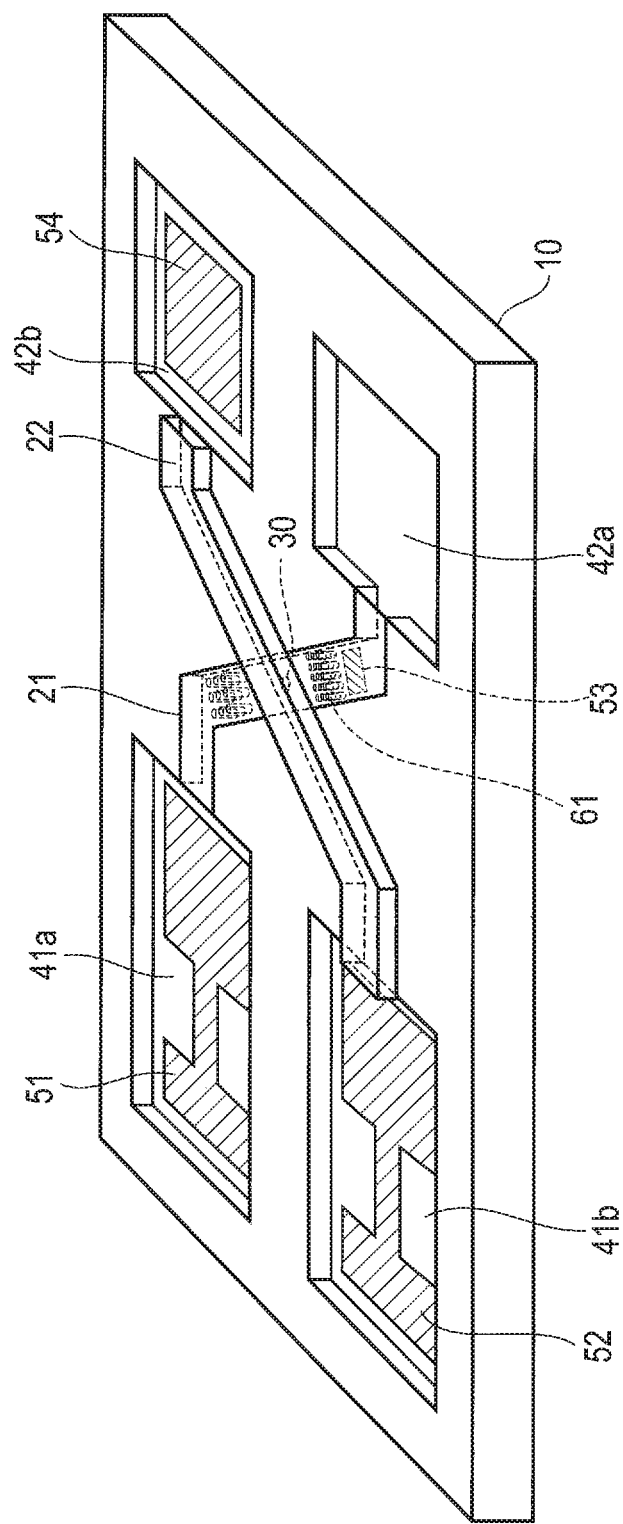
F I G. 8

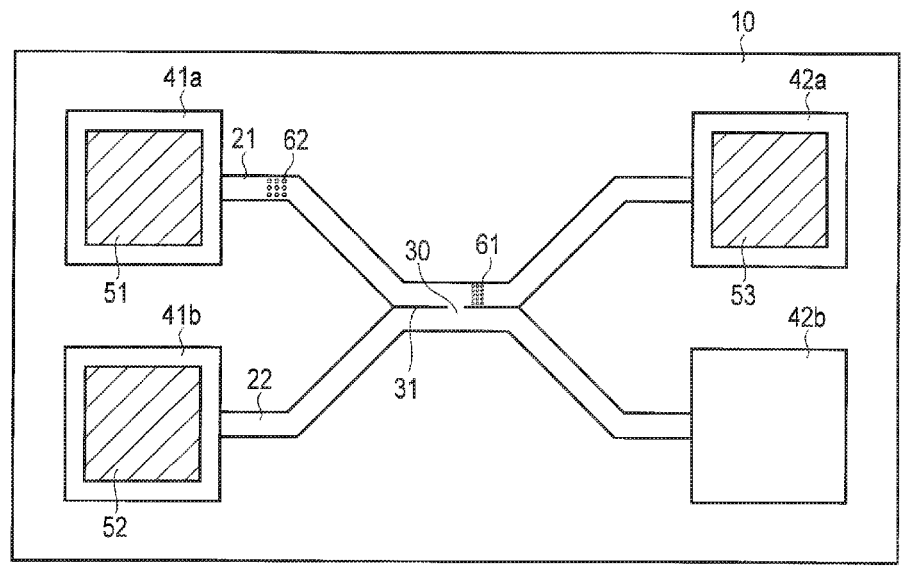
F I G. 11A
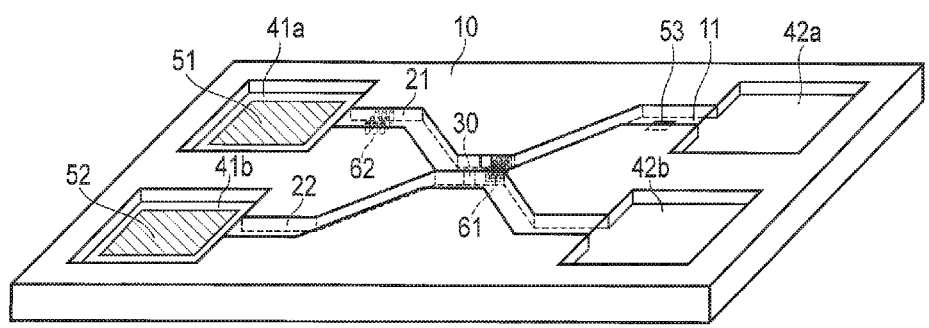
F I G. 11B

SEMICONDUCTOR ANALYSIS CHIP AND PARTICLE INSPECTION METHOD

CROSS-REFERENCE TO RELATED APPLICATIONS

This application is based upon and claims the benefit of priority from Japanese Patent Application No. 2015-179766, filed Sep. 11, 2015, the entire contents of which are incorporated herein by reference.

FIELD

Embodiments described herein relate generally to a semiconductor analysis chip for detecting particles in a sample liquid, and a particle inspection method using the chip.

BACKGROUND

In the fields of biotechnology and health care, attention has recently been paid to a semiconductor analysis chip wherein microfluidic device, such as a micro flow channel and a detection mechanism, are integrated. In this type of chips, a sample liquid is poured into a channel, and a change in an electrical signal is detected when a particle of the sample liquid passes through a micropore formed in the channel. From the change, a particle or biopolymer in the liquid can be detected.

BRIEF DESCRIPTION OF THE DRAWINGS

FIG. 2 is a schematic perspective view showing the schematic structure of the semiconductor analysis chip according to the first embodiment.

FIG. 3 is a schematic cross-sectional view showing the structure of the semiconductor analysis chip according to the first embodiment.

FIG. 6 is a schematic perspective view showing the schematic structure of a semiconductor analysis chip according to a second embodiment.

FIG. 7 is a schematic cross-sectional view showing the structure of the semiconductor analysis chip according to the second embodiment.

FIG. 8 is a schematic perspective view showing the schematic structure of a semiconductor analysis chip according to a third embodiment.

FIG. 11A is a plan view showing yet another modification.

FIG. 11B is a perspective diagram showing a further modification.

DETAILED DESCRIPTION

In general, according to one embodiment, a semiconductor analysis chip for detecting a particle in a sample liquid includes: a semiconductor substrate; a first flow channel provided in a surface portion of the semiconductor substrate and including an end portion of the first flow channel at a liquid introduction side and another end portion of the first flow channel at a liquid discharge side; a second flow channel provided in a surface portion of the semiconductor substrate and including an end portion of the second flow channel at a liquid introduction side and another end portion of the second flow channel at a liquid discharge side, part of the second flow channel contacting or intersecting the first flow channel; a micropore provided in a contact portion or an intersection of the first and second flow channels, and configured to permit the particle to pass therethrough; a first electrode provided in the first flow channel; a second electrode provided in the second flow channel; and a third electrode provided in the first flow channel downstream of the first electrode.

Referring to the accompanying drawings, semiconductor analysis chips according to embodiments will be described.

First Embodiment

Figure 1:
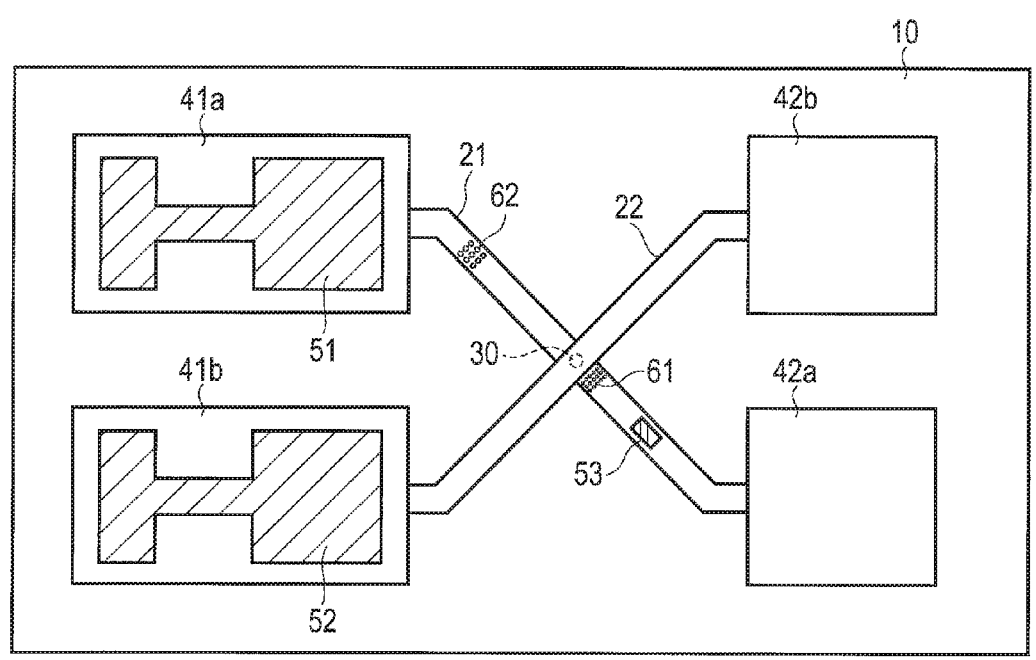
FIG. 1 is a schematic plan view showing the structure of the semiconductor analysis chip according to a first embodiment.

FIGS. 1 to 3 are views for schematically explaining the structure of a semiconductor analysis chip according to a first embodiment. FIG. 1 is a plan view, FIG. 2 is a perspective view, and FIG. 3 is a cross-sectional view taken along line I-I' in FIG. 2.

In the figures, reference number 10 denotes a semiconductor substrate. As the substrate 10, various semiconductor substrates formed of Si, Ge, SiC, GaAs, InP, GaN, etc., can be used. Hereinafter, a description will be given of an example of the semiconductor substrate 10, which is formed of Si.

A first flow channel 21 for permitting a sample liquid to flow, and a second flow channel 22 for permitting an electrolytic solution to flow, are formed in the surface of the Si substrate 10. Flow channels 21 and 22 intersect each other.

The first flow channel 21 is formed by etching the Si substrate 10 to have a width of, for example, 50 μm and a depth of, for example, 2 μm, and covering an upper portion thereof with an insulating film (with a thickness of, for example, 200 nm), such as a silicon oxide ($SiO_2$) film, a silicon nitride (SiNx) film or an alumina ($Al_2O_3$) film. That is, a passage cap layer 12 (serving as a lid for sealing the flow channel) is formed above the first flow channel 21, whereby the first flow channel 21 is formed as a slot type passage. Furthermore, the bottom and side of the first flow channel 21 are formed as a silicon oxide film 11 by oxidizing the Si substrate 10.

The second flow channel 22 is formed by using, as its bottom, a surface of the Si substrate 10 and the cap layer 12, and forming its upper and side surfaces thereof by an insulating film 13. Thus, the second flow channel 22 is formed as an insulating-film-tunnel type passage. More specifically, in order to form the second flow channel 22, a sacrifice layer of a desired pattern is formed on the substrate 10, and then the insulating layer 13, such as a silicon oxide film, is formed to cover the sacrifice layer. After that, the sacrifice layer is removed by ashing, etching, etc.

A micropore 30 permitting a particle 70 to flow therethrough is formed in an intersection between the first and second flow channels 21 and 22. Assume here that the size (diameter) of the micropore 30 is slightly larger than that of a particle to detect. If the size of the particle is 1 μm, the diameter of the micropore 30 is set, to, for example, 1.5 μm.

A first liquid-introduction reservoir 41a for receiving a sample liquid is formed on the liquid-introduction side of the first flow channel 21, and a first liquid-discharge reservoir 42a for discharging the sample liquid is formed on the liquid-discharge side of the first flow channel 21. A second liquid-introduction reservoir 41b for receiving an electrolytic solution is formed on the liquid-introduction side of the second flow channel 22, and a second liquid-discharge reservoir 42b for discharging the electrolytic solution is formed on the liquid-discharge side of the second flow channel 22. Each of reservoirs 41a, 41b, 42a and 42b is formed by etching, using selective etching, the surface of the Si substrate 10 to form, for example, a square recess having sides of 1 mm and a depth of 2 μm.

A first electrode 51 is provided in reservoir 41a, and a second electrode 52 is provided in reservoir 41b. Electrodes 51 and 52 are provided for detecting the particles 70, and are formed so that at least parts of them will be exposed to the interiors of the respective reservoirs. It is sufficient if the electrodes each have a liquid-contact surface formed of AgCl, Pt, Au, W, etc. One of these materials may be selected in accordance with the type of the sample liquid or the electrolytic solution. Further, the electrodes may not always be fixed in reservoirs. Particles can be also detected by inserting external electrodes into the respective flow channels to thereby bring them into contact with the sample liquid or the electrolytic solution in reservoirs.

A third electrode 53 is provided downstream of the micropore 30 of the first flow channel 21. More specifically, the third electrode 53 is provided on the silicon oxide 11 at a position downstream of a pillar array 61 described later. The third electrode 53 is provided for causing the sample liquid in the first flow channel 21 to act as an electroosmotic flow, when a voltage is applied between the first and third electrodes 51 and 53.

Figure 4:
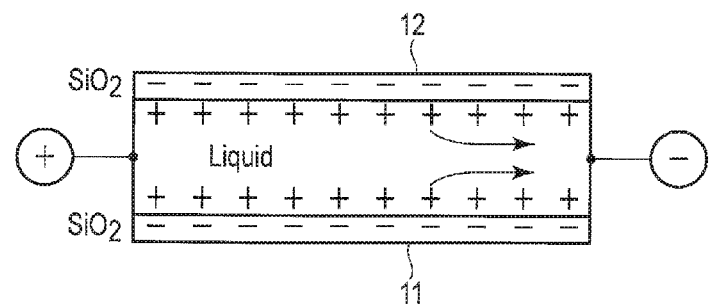
FIG. 4 is a schematic view for explaining an electroosmotic flow.

FIG. 4 is a sectional view taken along a flow in a flow channel, assumed when the inner surface of the flow channel is formed of $SiO_2$. When the flow channel is filled with the sample liquid or electrolytic solution, the $SiO_2$ inner surface is negatively charged. As a result, electrical static charge in the sample liquid or electrolytic solution is collected at the interfaces with the flow channel walls, whereby an electrical double layer is formed. At this time, if a voltage is applied between the opposite ends of the flow channel such that one of the ends assumes a positive potential and the other end assumes a negative potential, the electrical static charge at the interface between the flow channel wall and the sample liquid or electrolytic solution moves toward the negative potential. In accordance with this movement, the sample liquid or electrolytic solution starts to move. That is, a liquid flow occurs to the negative potential side.

A pillar array 61 formed by arraying, at regular intervals, pillars each extending from the bottom of the first flow channel 21 to the surface of the Si substrate 10 is provided downstream of the micropore 30 of the first flow channel 21. The pillar array 61 is a collector that collects and condenses the particles 70 to detect. The pillar array 61 is provided downstream of the micropore 30 such that the pillars are arranged at intervals at which the detection particles cannot be passed therethrough, and the electrolytic solution and particles smaller than the to-be-detected particles can be passed therethrough.

For example, if the detection particle diameter is 1 μm, the pillar array 61 is provided such that cylindrical pillars of diameter 1 μm or square pillars of side 1 μm are arranged across the first flow channel 21 at a maximum interval of 0.9 μm. The number of columns of the pillars of the pillar array 61 may be determined in consideration of the trap efficiency of detection particles. If, for example, ten columns of pillars of the pillar array 61 are arranged, particles having an outer diameter of 1.0 μm or more can be trapped substantially.

Moreover, pillar array 62 of a pillar gap greater than that of pillar array 61 is provided upstream of the micropore 30 of the first flow channel 21. Pillar array 62 functions as a filter for filtering particles of, for example, 5 μm or more. In this case, clogging of pillar array 61 with a giant particle can be easily avoided. This enables pre-processing, such as centrifugal separation or preliminary filtering of the sample liquid to be omitted, thereby simplifying a particle detection operation and shortening the time required for it.

In order to form pillar arrays 61 and 62, the Si substrate 10 is etched to leave a plurality of pillars in the first flow channel 21 when forming the first flow channel 21. Further, the pillars are oxidized when the substrate surface is oxidized (the bottom and side of the first flow channel 21 are oxidized).

The two flow channels 21 and 22 are filled with a sample liquid or electrolytic solution (i.e., a solution in which an electrolyte is melted to permit an ion current to flow), and a voltage is applied to the first and second electrodes 51 and 52. The current flowing at this time (a steady-state current flowing when no particles pass), i.e., the ion current passing through the micropore 30, changes in accordance with the opening size of the micropore 30. Further, when to-be-detected particles pass through the micropore 30, they block part of the micropore 30 to interfere with passing of ions, whereby the current flowing through the micropore is reduced accordingly. However, if the particles are conductive or surface-level conductive, there may be an increase in the ion current because of electrical conduction by the particles themselves. The change in the ion current is determined from the relationship between the shape, size, length, etc., of the micropore 30 and each particle. Thus, the state of the particles having passed through the micropore can be detected by observing, for example, changes in the ion current and changes in the ion current with time.

The polarities of the first and second electrodes 51 and 52 assumed when a voltage is applied therebetween are changed depending upon the charged state of to-be-detected particles (for example, bacteria, viruses and indicator particles). For instance, when detecting negatively-charged particles, ion current observation is performed, with the first and second electrodes 51 and 52 set as negative and positive poles, respectively. At this time, the particles are moved by an electric field in the liquid that occurs when a voltage is applied, and are passed through the micropore.

The opening size of the micropore 30 may be determined in consideration of easiness of passing of to-be-detected particles and a change (sensitivity) in the ion current. Specifically, it is set to, for example, 1.5 to 5 times the outer diameter of the to-be-detected particles. Further, as an electrolytic solution for dispersing the particles, an electrolytic solution, such as an aqueous KCl solution, or various buffer solutions, such as tris ethylene diamine tetra acetic acid (TE) buffer solution and phosphate buffered saline (PBS) solution, can be used.

In the semiconductor analysis chip of the first embodiment, a sample liquid (a suspending liquid obtained by dispersing to-be-detected particles in an electrolytic solution) is introduced into the liquid-introduction reservoir 41a of the first flow channel 21. Thus, the sample liquid flows into the first flow channel 21. On the other hand, the second flow channel 22 is used as an acceptance passage for the particles. An electrolytic solution containing no particles is introduced into the liquid-introduction reservoir 41b of the second flow channel 22, whereby the second flow channel 22 is filled with the electrolytic solution.

The particles are dammed up by nanopillar 61 in the first flow channel 21 in accordance with the flow of the sample liquid in the first flow channel 21, and pass through the micropore 30 promptly. At this time, the ion current flowing between the first and second electrodes 51 and 52 through the micropore 30 changes in accordance with the size of the micropore 30 and the size of the particles. This enables not only passing of the particles through the micropore 30, but also the size of the particles, to be detected.

However, when a voltage is applied between the first and second electrodes 51 and 52, an electroosmotic flow may occur in the first flow channel 21 in a direction opposite to the flow direction of the sample liquid, thereby interfering with the flow of the particles. Moreover, surface tension may occur at the interface between the first flow channel 21 and the liquid-discharge reservoir 42a of the first flow channel 21, thereby stopping the sample liquid having flowed through the first flow channel 21.

To avoid this, in the first embodiment, an electroosmotic flow in the same direction as the sample liquid is generated in the first flow channel 21 by arranging the third electrode 53 downstream of the micropore 30 of the first flow channel 21 and applying a suitable voltage between the first and third electrodes 51 and 53. That is, the flow of particles can be accelerated. Further, this electroosmotic flow enables the sample liquid in the first flow channel 21 to flow continuously. As a result, even if surface tension occurs in the liquid-discharge reservoir 42a of the first flow channel 21, the sample liquid can be discharged to the liquid-discharge reservoir 42a. For example, when the inner wall of the first flow channel 21 is formed of $SiO_2$, and the electrical resistance of the sample liquid or the electrolytic solution in the micropore 30 is high, the above-mentioned situation can be realized by setting, to V1>V3, the relationship between potential V1 of the first electrode 51 and potential V3 of the third electrode 53.

Furthermore, when the polarity of charged particles is negative, in order to pass particles through the micropore 30, it is desirable that the relationship between potentials V1 and V2 of the first and second electrodes be V1<V2. Also in this case, if V3<V1<V2, passing of particles through micropore can be realized, with the flow of the sample liquid maintained in the first flow channel 21. The relationship between V1, V2 and V3 can be freely set in accordance with the polarity of charged particles, and/or the material of the tunnel passages.

As a sequence of particle detection, the following method is possible: First, the sample liquid is dripped into the liquid-introduction reservoir 41a of the first flow channel 21, and is then introduced into the first flow channel 21. Subsequently, a voltage is applied between the first and third electrodes 51 and 53, thereby causing the sample liquid to sufficiently flow, utilizing an electroosmotic flow. On the other hand, the second flow channel 22 is filled with the electrolytic solution, whereby particles are collected in pillar array 61 in the first flow channel 21.

Subsequently, after stopping the application of the voltage between the first and third electrodes 51 and 53, a change in ion current occurring when a particle passes through the micropore 30 is measured by applying a voltage between the first and second electrodes 51 and 52. Since at this time, the application of the voltage between the first and third electrodes 51 and 53 is stopped, noise occurring when an ion current is measured between the first and second electrode 51 and 52 can be reduced. If such noise will not involve a problem, the voltage may be kept applied between the first and third electrodes 51 and 53.

Moreover, when particles are collected in pillar array 61, they may be adhered to pillar array 61, whereby the number of particles passing through the micropore 30 may decrease. In this case, if an inverse voltage is applied between the first and third electrodes 51 and 53, the particles adhered to pillar array 61 can be separated therefrom. Thus, the number of particles passing through the micropore 30 can be prevented from reduction, thereby enhancing the accuracy of detection.

Alternatively, the above-described detection can be performed with both the first and second flow channels filled with a sample liquid. This method can be utilized especially when the charged state of particles to detect is unknown, or when positively-charged particles and negatively-charged particles are mixed. Even when the charged state of particles is clear, detection may be performed, with the two flow channels filled with a sample liquid. In this case, it is not necessary to prepare both the sample liquid and the electrolytic solution, which simplifies detection operation of particles.

As described above, in the semiconductor analysis chip of the first embodiment, particle detection can be performed simply by introducing a sample liquid and performing electrical observation. This enables high sensitive detection of bacteria, viruses, etc., to be easily carried out. As a result, the analysis chip of the embodiment can be used for easy detection of epidemic bioagents or food-poisoning bacteria. In other words, the analysis chip can contribute to preventing expansion of epidemic diseases, or to securing food safety.

In addition, since in the first embodiment, an electroosmotic flow can be generated by applying a voltage between the third and first electrodes 53 and 51, the flow of the sample liquid in the first flow channel 21 can be further stabilized. Therefore, the number of particles passing through the micropore 30 can be prevented from reduction, thereby enhancing the accuracy of detection.

Figure 5:
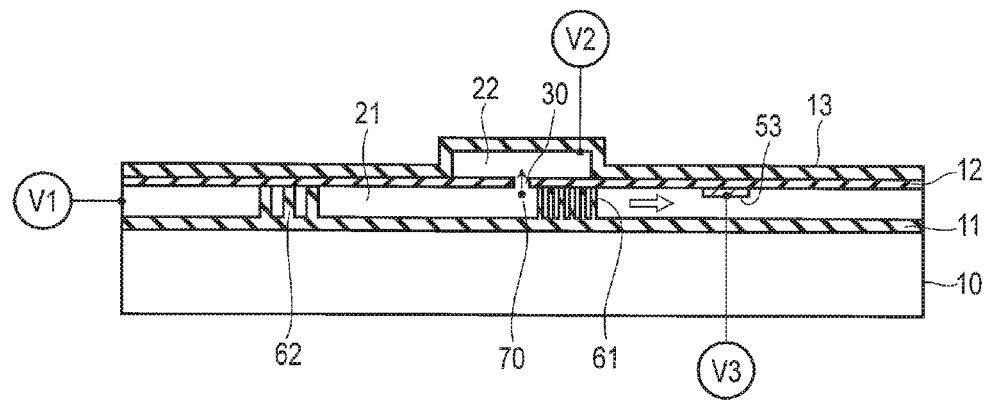
FIG. 5 is a cross-sectional view showing a modification of the first embodiment.

In addition, the third electrode 53 for generating an electroosmotic flow is not always provided on the bottom of the first flow channel 21, but may be provided on the ceiling wall of the first flow channel 21, as is shown in FIG. 5. Furthermore, it may be provided in the liquid-discharge reservoir 42a of the first flow channel 21.

Second Embodiment

FIGS. 6 and 7 are views for schematically explaining the structure of a semiconductor analysis chip according to a second embodiment. FIG. 6 is a perspective view, and FIG. 7 is a view taken along line II-II' in FIG. 6. In these figures, elements similar to those shown in FIGS. 1 to 3 are denoted by corresponding reference numbers, and no detailed description will be given thereof.

The second embodiment differs from the above-described first embodiment in that in the former, a fourth electrode 54 is provided in the liquid-discharge reservoir 42a of the first flow channel 21. By applying a voltage between the fourth and third electrodes 54 and 53, an electroosmotic flow can be generated therebetween. If the inner wall of the first flow channel 21 is charged with negative electricity, and if the inner wall of the first flow channel 21 is formed of, for example, $SiO_2$, an electroosmotic flow from the third electrode 53 to the fourth electrode 54 can be produced by setting, to V4<V3, the relationship between the respective potentials V3 and V4 of the third and fourth electrodes 53 and 54.

Application of a voltage between the first and third electrodes 51 and 53 can also generate an electroosmotic flow, as in the first embodiment. From the above, it is evident that setting of V4<V3<V1<V2 enables particles passing through the micropore 30 to be detected, with more reliable flow of the sample liquid in the first flow channel 21 realized.

Thus, the second embodiment can realize further enhancement of the detection efficiency of particles, in addition to the advantage of the first embodiment.

Third Embodiment

Figure 9:
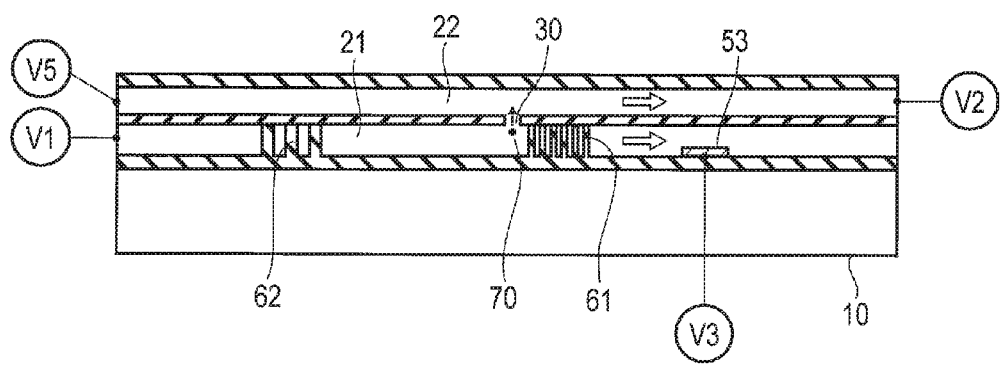
FIG. 9 is a schematic cross-sectional view showing the structure of the semiconductor analysis chip according to the third embodiment.

FIGS. 8 and 9 are schematic views for explaining the structure of a semiconductor analysis chip according to a third embodiment. FIG. 8 is a perspective view, and FIG. 9 is a cross-sectional view. In these figures, elements similar to those shown in FIGS. 1 to 3 are denoted by corresponding reference numbers, and no detailed description will be given thereof. In FIG. 9, in order to facilitate description, a cross section of the second flow channel 22 also taken along the flow is shown.

The third embodiment differs from the above-described first embodiment in that in the former, a fifth electrode 55 is provided in the liquid-discharge reservoir 42b of the second flow channel 22. By applying a voltage between the fifth and second electrodes 55 and 52, an electroosmotic flow can also be generated in the second flow channel 22. If the inner wall of the second flow channel 22 is charged with negative electricity, and if the inner wall of the second flow channel 22 is formed of, for example, $SiO_2$, an electroosmotic flow from the second electrode 52 to the fifth electrode 55 can be produced by setting, to V2>V5, the relationship between the respective potentials V2 and V5 of the second and fifth electrodes 52 and 55.

At this time, by setting V3<V1<V5<V2, a particle passing through the micropore 30 can be detected, with more reliable flow of the electrolytic solution in the second flow channel 22 realized.

(Modification)

The invention is not limited to the above-described embodiments.

Figure 10A:
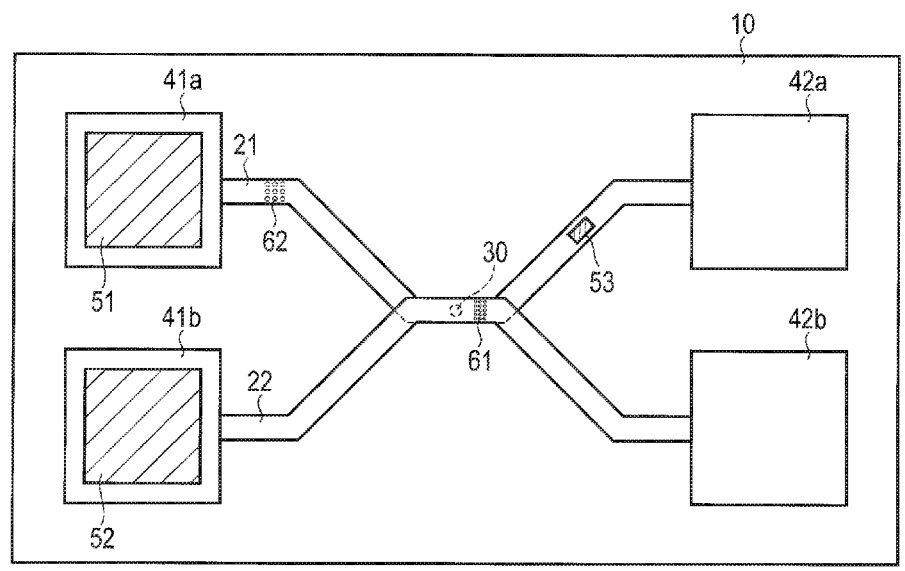
FIG. 10A is a plan view showing a modification.
Figure 10B:
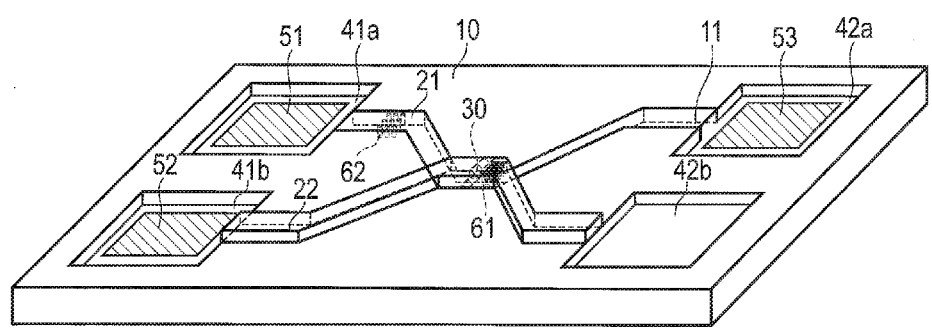
FIG. 10B is a perspective diagram showing another modification.

It is not always necessary to intersect the first and second flow channels each other. It is sufficient if parts of the flow channels contact each other, as is shown in the plan view of FIG. 10A and in the perspective view of FIG. 10B. In this case, the micropore 30 is formed in a contact portion (stacked portion) between the slot-like first flow channel 21 and the insulating-film-tunnel type second flow channel 22. Further, both the first and second flow channels may be slot-like passages, as is shown in the plan view of FIG. 11A and in the perspective view of FIG. 11B. In this case, a micropore 30 in the shape of a slit is formed in a contact portion between the first and second flow channels 21 and 22.

The third electrode 53 for generating an electroosmotic flow in the first flow channel 21 is not necessarily provided downstream of the micropore 30. It is sufficient if the position of the third electrode is downstream of the first electrode 51. Similarly, the fifth electrode 55 for generating an electroosmotic flow in the second flow channel 22 is not necessarily provided in the liquid-discharge reservoir 42b. It is sufficient if the position of the fifth electrode is downstream of the second electrode 52.

In the embodiments, the inner walls of the flow channels are negatively charged, and the particles are also negatively charged. However, if their charged states differ, potentials V1 to V5 of electrodes 51 to 55 are changed appropriately.

For example,

If the inner walls of the flow channels are negatively charged, and the particles are positively charged, the potentials of the first to fifth electrodes are such that V4<V3<V1 and

V5<V2<V1.

If the inner walls of the flow channels are positively charged, and the particles are negatively charged, the potentials of the first to fifth electrodes are such that V1<V3<V4 and

V1<V2<V5.

If the inner walls of the flow channels are positively charged, and the particles are also positively charged, the potentials of the first to fifth electrodes are such that V1<V3<V4 and

V2<V5<V1.

Moreover, the coatings of the inner walls of the flow channels are not necessarily limited to silicon oxide layers, but may be silicon nitride layers, or other insulating layers. If an inorganic layer, such as a silicon oxide or silicon nitride layer, is used as the coating of each inner wall of the flow channels, the coating can be made elaborate.

When forming a pillar array by oxidizing silicon in a silicon substrate as in the embodiments, the silicon oxide film on the inner wall of each flow channel can be easily formed simultaneously. When using a silicon nitride film, the coating of the inner wall of each flow channel can be formed as a strong film of a high Young's modulus by controlling its composition and/or process. Further, a highly vaporproof film can be formed easily. Furthermore, the coating of the inner wall of each flow channel may have a structure obtained by mixing or stacking a silicon oxide film and a silicon nitride film.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A semiconductor analysis chip for detecting a particle in a sample liquid, the chip comprising:
   a semiconductor substrate;
   a first flow channel provided in a surface portion of the semiconductor substrate and including a first end at a liquid introduction side and a second end at a liquid discharge side;
   a second flow channel provided in a surface portion of the semiconductor substrate and including a third end at a liquid introduction side and a fourth end at a liquid discharge side, part of the second flow channel contacting or intersecting the first flow channel;

a micropore provided in a contact portion or an intersection of the first and second flow channels, and configured to permit the particle to pass therethrough;
a first electrode provided in the first flow channel;
a second electrode provided in the second flow channel;
a third electrode provided in the first flow channel between the first electrode and the second end;
a first pillar and a second pillar arranged at a first distance from each other, and provided in the first flow channel; and
a third pillar and a fourth pillar arranged at a second distance from each other that is greater than the first distance, and provided in the first flow channel,
wherein the first end and the second end are located opposite to each other with respect to the micropore,
wherein the first pillar and the second pillar are provided on a side of the second end, and
wherein the third pillar and the fourth pillar are provided on a side of the first end.

2. The chip of claim 1, wherein the first distance is smaller than a diameter of the particle.

3. The chip of claim 1, wherein the semiconductor substrate comprises silicon, and an inner wall of the first flow channel, an inner wall of the second flow channel and surfaces of the first, second, third, and fourth pillars comprise silicon oxide.

4. The chip of claim 1, wherein the first electrode is provided on the side of the first end, and the third electrode is provided on the side of the second end.

5. The chip of claim 1, further comprising a first power source, a second power source, and a third power source, wherein a relationship between potential V1 of the first electrode provided by the first power source, potential V2 of the second electrode provided by the second power source, and potential V3 of the third electrode provided by the third power source is set to V3<V1<V2.

6. The chip of claim 1, further comprising a fourth electrode provided in the first flow channel, wherein the third electrode is provided between the micropore and the fourth electrode.

7. The chip of claim 1, further comprising a fourth electrode provided in the second flow channel.

8. The chip of claim 1, wherein the first and second flow channels include respective liquid-introduction reservoirs and respective liquid-discharge reservoirs.

9. The chip of claim 8, wherein:
the first electrode is provided in the liquid-introduction reservoir of the first flow channel;
the second electrode is provided in the liquid-introduction reservoir of the second flow channel; and
the third electrode is provided in the liquid-discharge reservoir of the first flow channel or between the liquid-discharge reservoir of the first flow channel and the micropore.

10. The chip of claim 1, wherein:
the first flow channel is a slot-like passage provided in the surface portion of the semiconductor substrate;
the second flow channel is an insulating-film-tunnel passage provided in the surface portion of the semiconductor substrate;
the first and second flow channels intersect each other; and
the micropore is provided at the intersection of the first and second flow channels.

11. The chip of claim 1, wherein:
the first and second flow channels are slot-like passages provided in the surface portions of the semiconductor substrate;
parts of the first and second flow channels contact each other; and
the micropore is provided at the contact portion of the first and second flow channels.

12. A semiconductor analysis chip for detecting a particle in a sample liquid, the chip comprising:
a semiconductor substrate;
a first flow channel provided in a surface portion of the semiconductor substrate and configured to receive the sample liquid;
a first liquid-introduction reservoir provided on a liquid-introduction side of the first flow channel;
a first liquid-discharge reservoir provided on a liquid-discharge side of the first flow channel;
a second flow channel provided in a surface portion of the semiconductor substrate and configured to receive the sample liquid or an electrolytic solution, part of the second flow channel contacting or intersecting the first flow channel;
a second liquid-introduction reservoir provided on a liquid-introduction side of the second flow channel;
a second liquid-discharge reservoir provided on a liquid-discharge side of the second flow channel;
a micropore provided in a contact portion or an intersection of the first and second flow channels, and configured to permit the particle to pass therethrough;
a first pillar and a second pillar arranged at a first distance from each other, and provided in the first flow channel;
a third pillar and a fourth pillar arranged at a second distance from each other that is greater than the first distance, and provided in the first flow channel;
a first electrode provided in the first liquid-introduction reservoir;
a second electrode provided in at least one of the second liquid-introduction reservoir and the second liquid-discharge reservoir; and
a third electrode provided in the first flow channel between the first liquid-introduction reservoir and the first liquid-discharge reservoir, or in the first liquid-discharge reservoir,
wherein the first flow channel includes a first end and a second end located opposite to each other with respect to the micropore,
wherein the first pillar and the second pillar are provided on a side of the first end, and
wherein the third pillar and the fourth pillar are provided on a side of the second end.

13. The chip of claim 12, wherein the first distance is smaller than a diameter of the particle.

14. The chip of claim 12, wherein the semiconductor substrate comprises silicon, and an inner wall of the first flow channel, an inner wall of the second flow channel and surfaces of the first, second, third, and fourth pillars comprise silicon oxide.

15. The chip of claim 12, further comprising a first power source, a second power source, and a third power source, wherein a relationship between potential V1 of the first electrode provided by the first power source, potential V2 of the second electrode provided by the second power source, and potential V3 of the third electrode provided by the third power source is set to V3<V1<V2.

16. The chip of claim 12, further comprising a fourth electrode provided in the first flow channel, wherein the third electrode is provided between the micropore and the fourth electrode.

17. A particle inspection method comprising:
using a semiconductor analysis chip for detecting a particle in a sample liquid, the semiconductor analysis chip including a semiconductor substrate, a first flow channel formed in a surface portion of the semiconductor substrate and configured to receive the sample liquid, a second flow channel formed in a surface portion of the semiconductor substrate and configured to receive the sample liquid or an electrolyte electrolytic solution, part of the second flow channel contacting or intersecting the first flow channel, a micropore formed in a contact portion or an intersection of the first and second flow channels, and configured to permit the particle to pass therethrough, a first electrode provided in the first flow channel, a second electrode provided in the second flow channel, and a third electrode provided in the first flow channel downstream of the first electrode;
introducing the sample liquid into the first flow channel;
introducing the sample liquid or the electrolytic solution into the second flow channel;
applying, between the first and third electrodes, a voltage for generating an electroosmotic flow, to accelerate flow of the sample liquid in the first flow channel and to move the particle from an upstream side to a downstream side; and
applying a voltage between the first and second electrodes to detect a change in a current when the particle passes through the micropore, in order to detect a presence of the particle.

18. The method of claim 17, wherein application of the voltage between the first and third electrodes is stopped before application of the voltage between the first and second electrodes.

* * * * *